United States Patent
Hoshina et al.

(10) Patent No.: US 9,376,456 B2
(45) Date of Patent: Jun. 28, 2016

(54) COMPOUND, DRYING AGENT, SEALING STRUCTURE, AND ORGANIC EL ELEMENT

(71) Applicant: Futaba Corporation, Mobara-shi, Chiba (JP)

(72) Inventors: Yusuke Hoshina, Mobara (JP); Yoshie Takakura, Mobara (JP)

(73) Assignee: FUTABA CORPORATION, Chiba (JP)

( * ) Notice: Subject to any disclaimer, the term of this patent is extended or adjusted under 35 U.S.C. 154(b) by 0 days.

(21) Appl. No.: 14/717,871

(22) Filed: May 20, 2015

(65) Prior Publication Data

US 2015/0368279 A1 Dec. 24, 2015

(30) Foreign Application Priority Data

May 22, 2014 (JP) ................. 2014-106378

(51) Int. Cl.
| | |
|---|---|
| *C07F 5/06* | (2006.01) |
| *C08K 5/56* | (2006.01) |
| *C08K 5/54* | (2006.01) |
| *H01L 51/00* | (2006.01) |
| *B01D 53/28* | (2006.01) |
| *C07C 53/15* | (2006.01) |
| *H05B 33/04* | (2006.01) |
| *H01L 51/52* | (2006.01) |

(52) U.S. Cl.
CPC ............ *C07F 5/069* (2013.01); *B01D 53/28* (2013.01); *C07C 53/15* (2013.01); *C08K 5/54* (2013.01); *C08K 5/56* (2013.01); *H01L 51/005* (2013.01); *H05B 33/04* (2013.01); *B01D 2253/20* (2013.01); *B01D 2257/80* (2013.01); *H01L 51/5246* (2013.01); *H01L 51/5259* (2013.01)

(58) Field of Classification Search
CPC .......... C07F 5/069; C07C 53/15; C08K 5/56; C08K 5/54; B01D 53/28; H01L 51/005; H05B 33/04

USPC .................... 556/182, 183; 428/704; 257/40; 106/481

See application file for complete search history.

(56) References Cited

FOREIGN PATENT DOCUMENTS

| | | |
|---|---|---|
| DE | 10 2013 100 956 | 8/2013 |
| JP | 9-035868 | 2/1997 |
| JP | 2013-176751 | 9/2013 |
| WO | WO 2014/046209 A1 * | 3/2014 |

OTHER PUBLICATIONS

Office Action issued in counterpart German Patent Application No. 102015209342.5, Feb. 26, 2016, 7 pages.

* cited by examiner

*Primary Examiner* — Porfirio Nazario Gonzalez
(74) *Attorney, Agent, or Firm* — Hamre, Schumann, Mueller & Larson, P.C.

(57) ABSTRACT

A compound represented by formula (1) is provided:

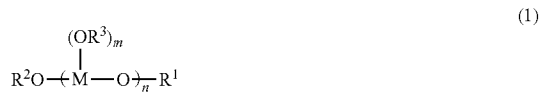

(1)

wherein M represents an aluminum atom, a titanium atom, a silicon atom, or a boron atom; m represents 1 or 2; n represents a positive integer; $R^1$, $R^2$ and $R^3$ each independently represent a C1-16 alkyl group optionally substituted with one or more fluorine atoms or a C2-17 acyl group optionally substituted with one or more fluorine atoms; and in the case where a plurality of $R^3$ is present, the plurality of $R^3$ may be the same or different to each other.

7 Claims, 3 Drawing Sheets

(a)

(b)

(c)

(d)

COMPOUND, DRYING AGENT, SEALING STRUCTURE, AND ORGANIC EL ELEMENT

TECHNICAL FIELD

The present invention relates to a compound as well as a drying agent, a sealing structure and an organic EL element using the same.

BACKGROUND

In recent years, research and development have been actively carried out regarding organic EL displays or organic EL lights that are light-emitting devices using an organic electroluminescence (EL) element. The organic EL element has a structure in which an organic layer, which is a thin film including an organic light-emitting material, is interposed between a pair of electrodes. The organic EL element is a self light-emitting element that uses light emission (fluorescence or phosphorescence) at the time of deactivation of excitons, which have been generated by recombination of holes and electrons injected into the thin film.

The most critical issue with the organic EL element is an improvement in the durability, and particularly, preventing non-light-emitting portions in the organic layer, which are called dark spots, from occurring and growing is the biggest issue. When the diameter of a dark spot grows to some tens of micrometers, non-light-emitting portions become visually observable. As a principal cause of the dark spots, the influence of moisture and oxygen is large, and it is known that moisture, even if in an extremely small amount, particularly exerts a large influence.

Therefore, methods for preventing moisture and oxygen from infiltrating into organic EL elements have been variously investigated. For example, in Patent Literature 1, a method involving providing a sealing layer composed of an inert liquid that contains an adsorbent around the circumference of an organic EL element in which an organic layer is laminated has been suggested.

Alternatively, for the purpose of physical protection of the organic layer, an improvement in the heat dissipation property and the like, a filled sealing structure in which an airtight container of the organic EL element is filled with a filler has been suggested, and additionally, a filled sealing structure that contains a drying agent as a filler also has been suggested. For example, in Patent Literature 2, a method involving using an organic metal compound that is a drying agent and has a predetermined structure together with a viscous substitution material such as silicone as filler has been suggested.

CITATION LIST

Patent Literature

[Patent Literature 1] JP H09-035868 A
[Patent Literature 2] JP 2013-176751 A

SUMMARY

Incidentally, a conventional organic metal compound that is used as a drying agent for organic EL elements and the like of the filled sealing structure has a property of dissolving organic layers in the organic EL elements. In the organic EL elements of the filled sealing structure, it is rare for a drying agent to come in a direct contact with an organic layer because the electrode formed from aluminum and the like comes in contact with the drying agent, but in the case where the drying agent comes in contact with the organic layer, there is a possibility that the drying agent penetrates the organic layer to cause dissolution of the organic layer. Since the dissolution of the organic layer becomes a cause of generating dark spots and leads to a leakage failure in the device, it is desired to use an agent as a drying agent that can suppress its penetration into the organic layer.

The present invention has been made in consideration of the problem described above, and has an object to provide a compound that has a sufficient water-trapping property and, when used as a drying agent, can suppress its penetration into an organic layer, as well as a drying agent, a sealing structure and an organic EL element using this compound.

The present invention provides a compound represented by formula (1):

[Chemical Formula 1]

(1)

wherein M represents an aluminum atom, a titanium atom, a silicon atom, or a boron atom; m represents 1 or 2; n represents a positive integer; $R^1$, $R^2$ and $R^3$ each independently represent a C1-16 alkyl group optionally substituted with one or more fluorine atoms or a C2-17 acyl group optionally substituted with one or more fluorine atoms, and in the case where a plurality of $R^3$ is present, the plurality of $R^3$ may be the same or different to each other;

a part of the carbon atoms composing the C1-16 alkyl group optionally substituted with one or more fluorine atoms may be replaced with one or more oxygen atoms, and a part of the carbon atoms composing the C2-17 acyl group optionally substituted with one or more fluorine atoms may be replaced with one or more oxygen atoms; and a proportion of the total number of the fluorine atoms in $R^1$, $R^2$ and $R^3$ is 15% or more relative to the total number of the fluorine atoms and hydrogen atoms in $R^1$, $R^2$ and $R^3$, and in the case where at least one of $R^1$, $R^2$ and $R^3$ is an acyl group substituted with one or more fluorine atoms, at least another one of $R^2$ and $R^3$ is an alkyl group substituted with one or more fluorine atoms.

The amount of water trapped per unit volume of the compound represented by formula (1) is high, and the compound is excellent in a water-trapping property. Additionally, since the compound contains fluorine atoms, whose compatibility with an organic layer is low, in a predetermined proportion, it becomes possible to suppress its penetration into the organic layer when used as a drying agent. Furthermore, since the compound represented by formula (1) is excellent in translucency and is not cracked and opacified after water trapping, the compound can be suitably applied to top-surface light-emission (top emission) type organic EL elements that extract light from a sealing substrate side described below.

The present invention also provides a drying agent that contains a compound represented by formula (1). It is preferable that the drying agent further contain a viscosity modifier.

The present invention provides a sealing structure, wherein a pair of substrates is sealed with a sealing agent, and the sealing structure comprises the drying agent therein.

The present invention also provides an organic EL element that comprises an element substrate, a sealing substrate disposed opposite to the element substrate, a laminate being provided on the element substrate and including an organic layer interposed between a pair of electrodes, and a sealing agent sealing outer peripheral parts of the element substrate and the sealing substrate, wherein a sealed space of the organic EL element is filled with the drying agent.

According to the present invention, a compound that is excellent in a water trapping property and can suppress its penetration to an organic layer when used as a drying agent, and as well as a drying agent, a sealing structure, and an organic EL element using this compound can be provided.

DETAILED DESCRIPTION

Figure 1:
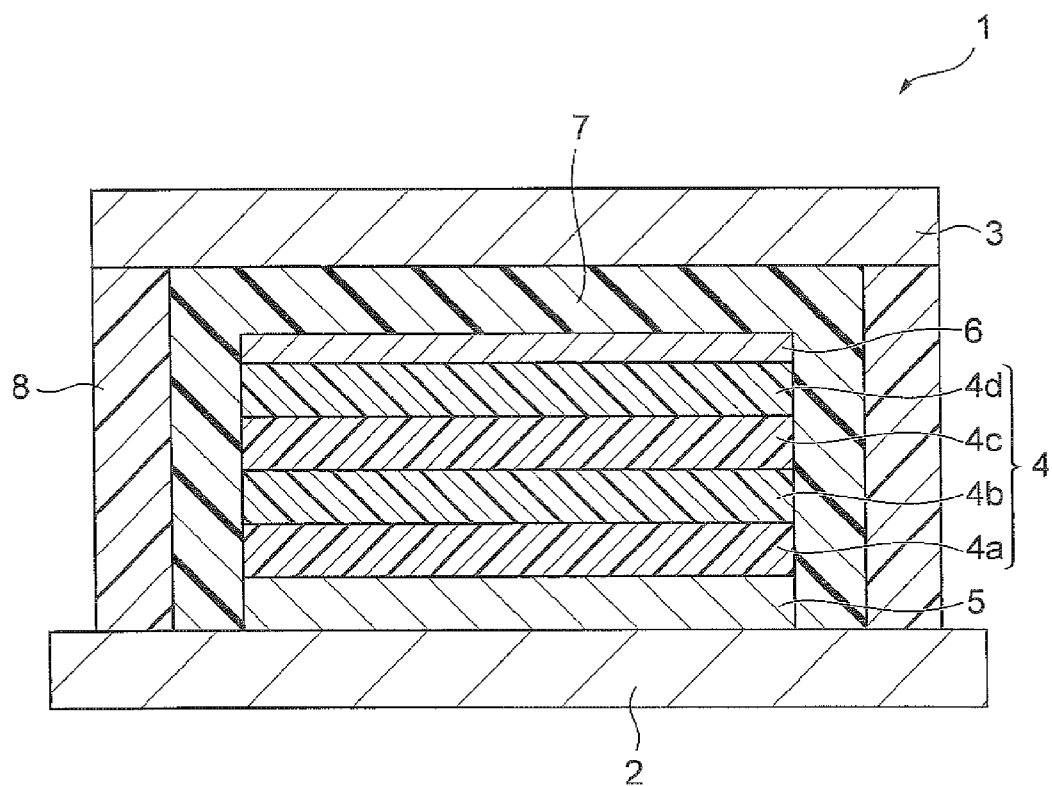
FIG. 1 is a schematic cross-sectional view illustrating the structure of an organic EL element according to one embodiment of the present invention.

Hereinbelow, one embodiment of the present invention will be described, but the present invention is not intended to be limited to this.

[Compound]

The compound according to the present embodiment is a compound represented by formula (1).

[Chemical Formula 2]

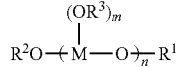

(1)

In formula (1), M represents an aluminum atom, a titanium atom, a silicon atom, or a boron atom, and it is preferable that M be an aluminum atom.

In formula (1), m represents the number of $OR^3$ groups in M and indicates 1 or 2. In the case where M is an aluminum atom or a boron atom, m is 1, and in the case where M is a titanium atom or a silicon atom, in is 2.

In formula (1), n represents the number of M in a molecule and indicates a positive integer. It is preferable that n be from 1 to 1000, it is more preferable that n be from 1 to 100, it is further preferable that n be from 1 to 10, and it is particularly preferable that n be 1.

In formula (1), $R^2$ and $R^3$ each independently represent a C1-16 alkyl group optionally substituted with one or more fluorine atoms or a C247 acyl group optionally substituted with one or more fluorine atoms, a linear or branched C1-12 alkyl group substituted with one or more fluorine atoms or a linear or branched C2-13 acyl group substituted with one or more fluorine atoms is preferred, and a linear or branched C2-8 alkyl group substituted with one or more fluorine atoms is more preferred. In the case where a plurality of $R^3$ is present, the plurality of $R^3$ may be the same or different to each other.

Examples of the C1-16 alkyl group include linear, branched or cyclic alkyl groups and specifically include a methyl group, an ethyl group, a n-propyl group, an isopropyl group, a n-butyl group, an isobutyl group, a sec-butyl group, a tert-butyl group, a n-pentyl group, an isopentyl group, a sec-pentyl group, a neopentyl group, a n-hexyl group, a cyclohexyl group, a n-heptyl group, a n-octyl group, a nonyl group, a decanyl group, a dodecanyl group, a tetradecanyl group, and a hexadecanyl group.

The C1-16 alkyl group optionally substituted with one or more fluorine atoms means the C1-16 alkyl group and a C1-16 alkyl group in which any hydrogen atom is replaced with one or more fluorine atoms. In the C1-16 alkyl group substituted with one or more fluorine atoms, all the hydrogen atoms may be replaced with fluorine atoms, and only a part of the hydrogen atoms may be replaced with fluorine atoms. In the case where only a part of the hydrogen atoms are replaced with fluorine atoms, it is preferable that the hydrogen atoms on the terminal carbon atom in the alkyl group are all replaced with fluorine atoms.

Examples of the C1-16 alkyl group substituted with one or more fluorine atoms include a difluoromethyl group, a trifluoromethyl group, a 2,2-difluoroethyl group, a 2,2,2-trifluoroethyl group, a 3,3,3-trifluoropropyl group, a heptafluoropropyl group, a 3,3,4,4,5,5,6,6,6-nonafluorohexyl group, and a 2,2,3,3,4,4,5,5,6,6,7,7,7-tridecafluoroheptyl group. The proportion of the fluorine atom in the alkyl group substituted with one or more fluorine atoms is not particularly limited, but it is preferably 40% or more, more preferably 50% or more, and further preferably 60% or more, relative to the total number of the fluorine atoms and hydrogen atoms in the alkyl group substituted with one or more fluorine atoms.

The C2-17 acyl group optionally substituted with one or more fluorine atoms means a group represented by $R^4$—CO—. $R^4$ herein indicates a C1-16 alkyl group optionally substituted with one or more fluorine atoms. Examples of the C1-16 alkyl group optionally substituted with one or more fluorine atoms in $R^4$ include those similar to the C1-16 alkyl group optionally substituted with one or more fluorine atoms in the $R^1$, $R^2$ and $R^3$.

A part of the carbon atoms composing the C1-16 alkyl group optionally substituted with one or more fluorine atoms may be replaced with one or more oxygen atoms. Examples of the alkyl group optionally substituted with such an oxygen group include a trifluoromethoxymethyl ($CF_3OCH_2$) group, a $CF_3OCF_2CF_2OCF_2CH_2$ group, a $CF_3O(CF_2CF_2O)_2CF_2CH_2$ group, a $CF_3CF_2CF_2CF_2OCF_2CF_2OCF_2CH_2$ group, and a $CF_3CF_2CF_2CF_2O(CF_2CF_2O)_2CF_2CH_2$ group. Alternatively, a part of the carbon atoms composing the C2-17 acyl group optionally substituted with one or more fluorine atoms may be replaced with one or more oxygen atoms. Examples of the acyl group optionally substituted with one or more oxygen atoms include those that have a group similar to an alkyl group optionally substituted with one or more oxygen atoms as $R^4$. The number of the carbon atoms to be replaced with one or more oxygen atoms can be, for example, from 0 to 5, preferably 0 or 1. In the case where a plurality of the carbon atoms is replaced with one or more oxygen atoms, it is preferable that oxygen atoms be not adjacent to one another.

In formula (1), the proportion of the total number of the fluorine atoms in $R^1$, $R^2$ and $R^3$ is 15% or more relative to the total number of the fluorine atoms and hydrogen atoms in $R^1$, $R^2$ and $R^3$. The proportion of the total number of the fluorine atoms in $R^1$, $R^2$ and $R^3$ is preferably 30% or more, more preferably 40% or more, and further preferably 50% or more, relative to the total number of the fluorine atoms and hydrogen atoms in $R^1$, $R^2$ and $R^3$. It should be noted that the hydrogen atoms in the alkyl group or the acyl group in $R^1$, $R^2$ and $R^3$ may be all replaced with one or more fluorine atoms.

In the case where at least one of $R^1$, $R^2$ and $R^3$ in formula (1) is an acyl group substituted with one or more fluorine atoms, at least another one of $R^1$, $R^2$ and $R^3$ is an alkyl group substituted with one or more fluorine atoms.

The compound represented by formula (1) may form an association compound of compounds represented by formula (1).

Suitably specific examples of the compound represented by formula (1) include compounds represented by the formulas (1A), (1B), (1C), (1D), and (1E) shown hereinbelow.

[Chemical Formula 3]

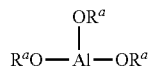 (1A)

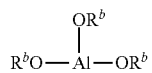 (1B)

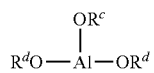 (1C)

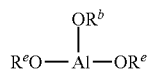 (1D)

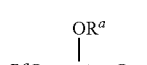 (1E)

wherein $R^a$ represents a 2,2,3,3,4,4,5,5,6,6,7,7,7-tridecafluoroheptyl group, $R^b$ represents a 2,2,2-trifluoroethyl group, $R^e$ represents a heptafluorobutanoyl group, $R^d$ represents a sec-butyl group, and $R^e$ represents an isopropyl group.

It should be noted that the proportions of the total number of the fluorine atoms in the compounds represented by the formulas (1 A), (1B), (1C), (1D), and (1E) each are 87%, 60%, 28%, 16%, and 87% relative to the total number of the fluorine atoms and hydrogen atoms.

According to the compound represented by formula (1), it is possible to allow the amount of water trapped per unit volume to be, for example, more than 70 mg/cm$^3$, preferably 80 mg/cm$^3$ or more.

[Process of Manufacturing the Compound]

It is possible to obtain the compound represented by formula (1) by, for example, allowing a compound having M or a simple substance of M to react with an alcohol having $R^1$, $R^2$ or $R^3$, or a carboxylic acid having $R^4$. The alcohol and carboxylic acid herein correspond respectively to the C1-16 alkyl group optionally substituted with one or more fluorine atoms and the C2-17 acyl group optionally substituted with one or more fluorine atoms in formula (1).

In the case where M is an aluminum atom, examples of the compound having M include aluminum tri-n-butoxide, aluminum tri-sec-butoxide, aluminum tri-tert-butoxide, aluminum tri-n-octoxide, aluminum tri-sec-octoxide, aluminum tri-n-dodecoxide, aluminum tri-sec-dodecoxide, aluminum trihydride, and lithium aluminum tetrahydride. In the case where M is a titanium atom, examples of the compound having M include titanium tetra-n-butoxide, titanium tetra-sec-butoxide, titanium tetra-tert-butoxide, titanium tetra-n-octoxide, titanium tetra-sec-octoxide, titanium tetra-n-dodecoxide, titanium tetra-sec-dodecoxide, and titanium tetrahydride. In the case where M is a silicon atom, examples of the compound having include tetra-n-butoxysilane, tetra-sec-butoxysilane, tetra-tert-butoxysilane, tetra-n-octoxysilane, tetra-sec-octoxysilane, tetra-n-dodecoxysilane, tetra-sec-dodecoxysilane, and silane. In the case where M is a boron atom, examples of the compound having M include tri-n-butyl borate, tri-sec-butyl borate, tri-tert-butyl borate, tri-n-octoxide borate, tri-sec-octoxide borate, tri-n-dodecoxide borate, tri-sec-dodecoxide borate, sodium tetrahydroborate, and diborane.

Examples of the alcohol having $R^1$, $R^2$ or $R^3$ include specifically methanol, ethanol, n-propyl alcohol, isopropyl alcohol, n-butyl alcohol, isobutyl alcohol, sec-butyl alcohol, tert-butyl alcohol, n-pentyl alcohol, isopentyl alcohol, sec-pentyl alcohol, neopentyl alcohol, n-hexyl alcohol, cyclohexanol, n-heptyl alcohol, n-octyl alcohol, nonyl alcohol, decanyl alcohol, tetradecanyl alcohol, hexadecanyl alcohol, difluoro methanol, trifluoro methanol, 2,2-difluoro-1-ethanol, 2,2,2-trifluoro-1-ethanol, 3,3,3-trifluoro-1-propanol, 3,3,4,4,5,5,6,6,6-nonafluoro-1-hexanol, and 2,2,3,3,4,4,5,5,6,6,7,7,7-tridecafluoro-1-heptanol.

The carboxylic acid having $R^4$ is a carboxylic acid represented by $R^4$COOH. Examples of the carboxylic acid having $R^4$ include those formed by replacing a hydroxyl group in an alcohol exemplified as the alcohol having the $R^1$, $R^2$ or $R^3$, with a carboxyl group.

Compounds having M or a simple substance of M, alcohols having $R^1$, $R^2$ or $R^3$, or carboxylic acids having $R^4$ each may be used singly or may be used in combination of two or more, but it is preferable to use each one singly.

The ratio when a compound having M or a simple substance of M reacts with an alcohol having $R^1$, $R^2$ or $R^3$, or a carboxylic acid having $R^4$ may be at least 3 mol or more of the alcohol having $R^1$, $R^2$ or $R^3$ or the carboxylic acid having $R^4$ with respect to 1 mol of the compound having M or the simple substance of M, but it is preferably possible to allow the alcohol having $R^1$, $R^2$ or $R^3$ or the carboxylic acid having $R^4$ to be from 3 to 9 mol.

A diol or dicarboxylic acid may be mixed in an arbitrary ratio to be allowed to react as a component other than the compounds having M, the simple substance of M, alcohols having $R^1$, $R^2$ or $R^3$, or carboxylic acids having $R^4$.

Examples of the diol herein include those formed by replacing one of the hydrogen atoms on the carbon atom of alcohol having the $R^1$, $R^2$ or $R^3$ with a hydroxyl group. Examples of the dicarboxylic acid include those formed by replacing two hydroxyl groups in a diol with carboxylic groups.

The reaction conditions can be selected as appropriate depending on the raw materials to be used, but it is preferable to perform heating and stirring in the absence or presence of a solvent at 40 to 150° C. and for 0.5 to 48 hours. Additionally, it is possible to distill the volatile component off under reduced pressure after the reaction is finished.

[Drying Agent]

The drying agent of the present embodiment contains a compound represented by formula (1).

It is preferable that the drying agent of the present embodiment further contain a viscosity modifier. By allowing the viscosity modifier to be contained, it is possible to modify the viscosity of the drying agent to thereby facilitate filling of the drying agent into the sealing structure.

Examples of the viscosity modifier include, as silicones, dimethyl silicones, methylphenyl silicones, alkyl-modified silicones, polyether-modified silicones, and fluorosilicones, and it is preferable to use a fluorosilicones. Alternatively, a perfluoro polyether may be used as the viscosity modifier.

The proportion of the viscosity modifier contained may be, for example, from 0.05 to 20-fold with respect to the mass of the compound represented by formula (1).

The drying agent of the present embodiment can contain components other than the compound represented by formula (1) and the viscosity modifier as long as the effects according to the present application invention are not impaired. Examples of the other components include conventionally-known drying agents, for example, chemical adsorbents such as calcium oxide and physical adsorbents such as zeolite and silica gel.

It is possible to apply the drying agent of the present embodiment on the target by a dispense application method, a One-Drop-Fill (ODF) method, a screen printing method, a spraying method, a hot-melt method and the like. In the case of applying a dispense application method, the viscosity of the drying agent is preferably from 1 to 5000 Pa·s, more preferably from 1 to 1000 Pa·s, and more preferably from 1 to 300 Pa·s. Alternatively, in the case of applying an ODF method, the viscosity of the drying agent is preferably from 0.1 to 1 Pa·s.

Since the drying agent of the present embodiment contains the compound represented by formula (1) that comprises fluorine atoms, whose compatibility with an organic layer is low, in a predetermined proportion, it becomes possible to suppress its penetration to the organic layer.

[Sealing Structure]

The sealing structure of the present embodiment is a sealing structure, wherein a pair of substrates is sealed with a sealing agent, and the sealing structure comprises the drying agent in the sealing structure. The drying agent may be applied to a part of a sealed space, for example, only to a predetermined area on the substrates or may fill the sealed space.

The sealing structure of the present embodiment can be suitably used especially when a device susceptible to moisture is sealed. Examples of such a device include organic electronic devices such as organic EL elements, organic semiconductors, and organic solar cells.

[Organic EL Element]

One embodiment of the organic EL element of the present invention will be described hereinbelow with reference to FIG. 1.

An organic EL element 1 of the present embodiment is an organic EL element of a filled sealing structure composed of an element substrate 2, a sealing substrate 3 disposed opposite to the element substrate 2, a laminate being provided on the element substrate 2 and including an organic layer 4 interposed between a pair of electrodes 5 and 6, a sealing agent 8 sealing outer peripheral parts of the element substrate 2 and the sealing substrate 3, and a filler 7 that fills the sealed space. The filler 7 is the drying agent of the present embodiment described above.

In the organic EL element 1, components conventionally known can be used as the components other than the filler 7, and one example thereof will be briefly described hereinbelow.

The element substrate 2 is composed of a rectangular glass substrate having an insulation property and translucency, and an anode (electrode) 5 of Indium Tin Oxide (ITO), which is a transparent electrically conductive material, is formed on this element substrate 2. This anode 5 is formed by patterning an ITO film deposited on the element substrate 2 by a Physical Vapor Deposition (PVD) method such as a vacuum deposition method and a sputtering method into a predetermined pattern shape by means of etching in accordance with a photoresist method. A part of the anode 5 as an electrode is connected to a driving circuit (not shown) pulled out to an end of the element substrate 2.

On the top surface of the anode 5, an organic layer 4, which is a thin film including an organic light-emitting material, is laminated by a PVD method, such as a vacuum deposition method and a resistance heating method. The organic layer 4 may be formed of a single layer or may be formed of a plurality of layers of different functions. The organic layer 4 in the present embodiment is a four-layer structure in which a hole-injection layer $4a$, a hole-transport layer $4b$, a light-emitting layer $4c$, and an electron-transport layer $4d$ are laminated in sequence from the anode 5 side. The hole-injection layer $4a$ is formed from copper phthalocyanine (CuPc) of a film thickness of some tens of nanometers, for example. The hole-transport layer $4b$ is formed from bis[N-(1-naphthyl)-N-phenyl]benzidine (α-NPD) of a film thickness of some tens of nanometers, for example. The light-emitting layer $4c$ is formed from tris(8-quinolinato)aluminum ($Alq_3$) of a film thickness of some tens of nanometers, for example. The electron-transport layer $4d$ is formed from lithium fluoride (LiF) of a film thickness of several nanometers, for example. Then, a light emitting portion is formed of the laminate in which the anode 5, the organic layer 4, and a cathode 6 described below are laminated in this order.

On the top surface of the organic layer 4 (electron-transport layer $4d$), a cathode (electrode) 6, which is a metal thin film, is laminated by a PVD method such as a vacuum deposition method. Examples of the metal thin film include simple substances of metal whose work function is small, such as Al, Li, Mg, and In, and alloys whose work function is small, such as Al—Li and Mg—Ag. The cathode 6 is formed in a film thickness from some tens of nanometers to some hundreds of nanometers (preferably from 50 nm to 200 nm). A part of the cathode 6 is pulled out to an end of the element substrate 2 and connected to the driving circuit (not shown).

The sealing substrate 3 is disposed in a manner to be opposed to the element substrate 2 with the organic layer 4 interposed therebetween, and the circumference of the element substrate 2 and the sealing substrate 3 are sealed with a sealing agent 8. As the sealing agent, an ultraviolet curing resin can be used. Additionally, in the sealed space, a filler 7, which is the drying agent of the present embodiment, is filled. This protects the organic layer 4 and the like.

It should be noted that although the organic EL element is a bottom-emission type organic EL element that extracts light from the element substrate side, the organic EL element of the present invention may be a top-emission type organic EL element that extracts light from the sealing substrate side. Top-emission type organic EL elements also can be manufactured by conventionally-known methods, but modifications such as use of a transparent electrode as the cathode 6 or exchange of the positions of the anode 5 and the cathode 6 become required in addition to using a substrate having translucency as the sealing substrate 3. Since the drying agent of the present embodiment is excellent in translucency and is not cracked and opacified after water trapping, it can be particularly suitably used in this top-emission type organic EL element.

[Method for Manufacturing the Organic EL Element]

Figure 2:
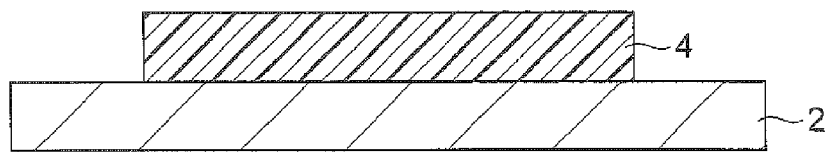
FIG. 2 is a schematic cross-sectional view illustrating a process of manufacturing the organic EL element according to one embodiment of the present invention.
Figure 2:
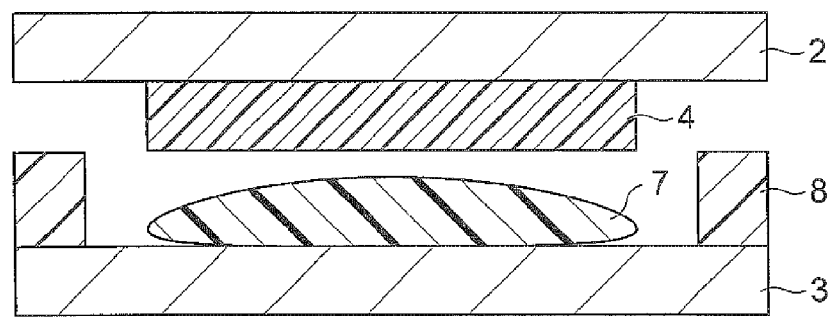
Figure 2:
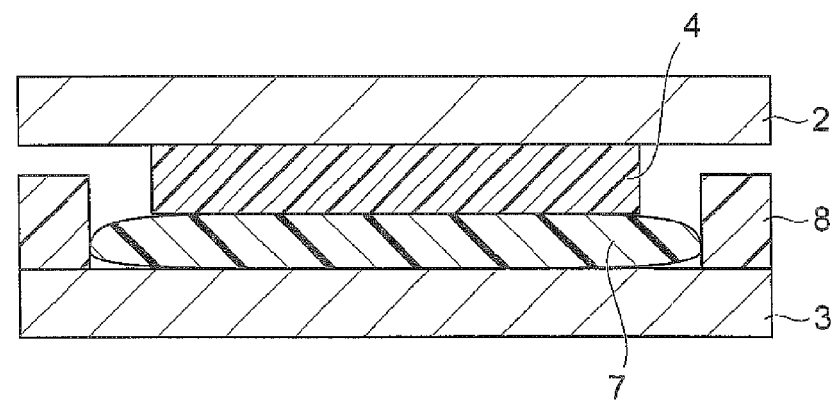
Figure 2:
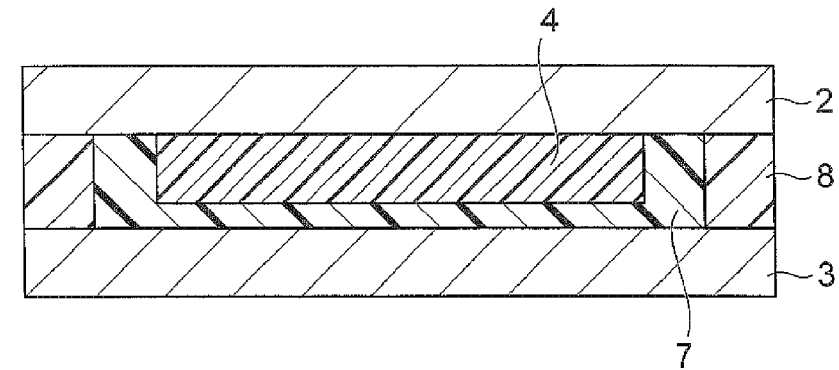

A process of manufacturing the organic EL element, particularly a sealing process will be described with reference to FIG. 2 hereinbelow.

First, a laminate in which an organic layer 4 and the like (electrodes are not shown) are laminated on an element substrate 2 is provided (FIG. 2(a)).

Subsequently, on a sealing substrate 3 separately provided, the drying agent of the present embodiment in a volume that can be filled into a space to be sealed is applied with a dispenser. Furthermore, a sealing agent 8 is applied with a dispenser so as to enclose the drying agent applied on the sealing substrate 3 (FIG. 2(b)). It is preferable to carry out these operations in a glove box purged with nitrogen whose dew point is −76° C. or less.

Subsequently, the element substrate 2 on which the organic layer 4 and the like are laminated and the sealing substrate 3 are bonded to each other (FIG. 2(c)). An organic EL element of the present embodiment is manufactured by sealing the bonded substrates with UV irradiation and heating at about 80° C. (FIG. 2(d)).

EXAMPLES

The present invention will be described more specifically hereinbelow, referring to examples. However, the present invention is not intended to be limited to these examples.

It should be noted that, in the examples, the viscosity, the water-trapping capacity, and the amount of water trapped per unit volume were measured according to the following methods.

(Viscosity)

A HBDV-E type digital viscometer manufactured by Brookfield Inc. was used to measure the viscosity at 25° C.

(Water-Trapping Capacity and Amount of Water Trapped Per Unit Volume)

To hydrous ethanol whose water content is 5% by mass, a sample was added so as to allow the sample concentration to be 10% by mass. After this was stirred for one minute, centrifugation was additionally conducted under conditions of 2000 rpm and 10 minutes. By use of a Karl-Fischer method moisture meter (CA-100, VA-100: vaporization method), the change in the water content of the ethanol after centrifugation was calculated as the amount of water trapped, and the water-trapping capacity and the amount of water trapped per unit volume were calculated according to the following formulas.

Water-trapping capacity [wt %]=Amount of water trapped [mg]/Amount of the sample [mg]×100

Amount of water trapped per unit volume [mg/cm$^3$]=Amount of water trapped [mg]/Sample volume [cm$^3$]

Sample volume [cm$^3$]=Sample amount [g]/Sample density [g/cm$^3$]

Preparation of the Compound

Example 1-1

To an eggplant flask, 31.4 g (0.127 mol) of aluminum tri-sec-butoxide and 147.4 g (0.421 mol) 1H,1H-tridecafluoro-1-heptanol (2,2,3,3,4,4,5,5,6,6,7,7,7-tridecafluoro-1-heptanol) were added and stirred with heating at 100° C. for an hour. By distilling the volatile component off under reduce pressure at 150° C. and 500 Pa, 116 g of a liquid compound was obtained. The viscosity of the compound obtained was 15 Pa·s, and the water-trapping capacity was 5 wt %. Additionally, the density of the compound obtained was 1.8 g/cm$^3$, and the amount of water trapped per unit volume was 90 mg/cm$^3$.

Example 1-2

To an eggplant flask, 12.1 g (0.05 mol) of aluminum tri-sec-butoxide and 10.5 g (0.05 mol) of heptafluoro butyrate were added and stirred with heating at 100° C. for an hour. By distilling the volatile component off under reduce pressure at 150° C. and 300 Pa, 16.1 g of a white solid compound was obtained.

Example 1-3

To an eggplant flask, 52.9 g (0.21 mol) of aluminum tri-sec-butoxide, 247 g (0.711 mol) 1H,1H-tridecafluoro-1-heptanol (2,2,3,3,4,4,5,5,6,6,7,7,7-tridecafluoro-1-heptanol), and 1.53 g (0.09 mol) of water were added and stirred with heating at 100° C. for an hour. By distilling the volatile component off under reduce pressure at 150° C. and 280 Pa, 159 g of a liquid compound was obtained.

Preparation of the Drying Agent

Comparative Example 1

A 48% solution of aluminum oxide octylate oligomer, which is an organic aluminum compound (product name: Olipe AOO, manufactured by Hope Chemical Co., Ltd.), and silicone (dimethyl silicone, product name: TSF451-100, manufactured by Momentive Performance Materials Japan LLC) were used. These were weighed such that the organic aluminum compound is 85% by mass and the silicone is 15% by mass, and mixed and stirred in an eggplant flask. By distilling the volatile component off under reduce pressure, a drying agent was obtained. The density of the drying agent was 1.0 g/cm$^3$, the water-trapping capacity was 7 wt %, and the amount of water trapped per unit volume was 70 mg/cm$^3$.

Storage Test in an 85° C. Environment

Example 2

First, on an element substrate, an anode of ITO as an electrically conductive material having transparency at a film thickness of 140 nm was deposited by a sputtering method and further patterned into a predetermined pattern shape by etching in accordance with a photoresist method to thereby form an anode.

Subsequently, copper phthalocyanine (CuPc) as the hole-injection layer formed by a resistance heating method in a film thickness of 70 nm on the top surface of the anode, bis[N-(1-naphthyl)-N-phenyl]benzidine (α-NPD) as the hole-transport layer deposited in a film thickness of 30 nm on the top surface of the hole-injection layer, and tris(8-quinolinato)aluminum (Alq$_3$) as the light-emitting layer in a film thickness of 50 nm deposited on the top surface of the hole-transport layer were deposited. Furthermore, lithium fluoride (LiF) as the electron-transport layer deposited in a film thickness of 7 nm on the top surface of the light-emitting layer was deposited, and furthermore, aluminum as the cathode in a film thickness of 150 nm was physically vapor-deposited.

Subsequently, in a glove box purged with nitrogen whose dew point is −76° C. or less, the compound of Example 1-1 as the drying agent only in a volume measured in advance that can be filled in a container was applied with a dispense on the sealing substrate. Subsequently, a sealing agent composed of an ultraviolet curing resin was applied with a dispense so as to enclose the drying agent filled on the sealing substrate.

Then, the element substrate on which the anode, the organic layer, and the cathode were laminated and the sealing substrate were bonded, and then sealed by ultraviolet irradiation and heating at 80° C. to thereby obtain an organic EL element of a filled sealing structure in which an airtight container is filled with the drying agent (the compound of Example 1-1). A hole was provided by laser on the cathode of the organic EL element, which was left under conditions of 85° C., and the dissolution distance of the organic layer was observed with an optical microscope. It should be noted that the dissolution distance represents a distance from the center of the hole to the end of a part where dissolution of the organic layer occurred.

Comparative Example 2

An organic EL element was obtained in the same manner as in Example 2 except that the drying agent of Comparative Example 1 was used instead of the compound of Example 1-1. A hole was provided by laser on the cathode of the organic EL element, which was left under conditions of 85° C., and the dissolution distance of the organic layer was observed with an optical microscope.

Figure 3:
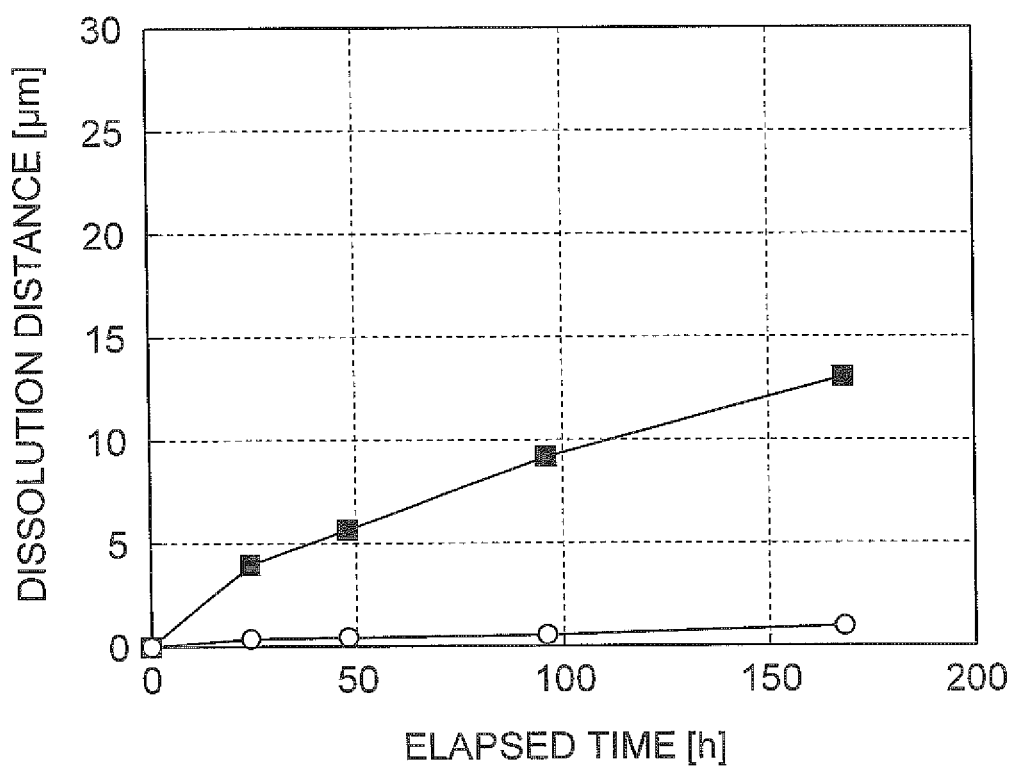
FIG. 3 is a graph that shows a relationship between the elapsed time and the dissolution distance of the organic layer in a storage test in an 85° C. environment.

The relationship between the elapsed time and the dissolution distance of the organic layer in the storage test in an 85° C. environment is shown in FIG. 3. The white circle plot indicates the dissolution distance when the compound of the Example 1-1 was used as the drying agent. The black square plot indicates the dissolution distance when the drying agent of the Comparative Example was used. According to FIG. 3, it was found that the dissolution distance is smaller and thus the penetration to the organic layer was more suppressed in the case where the compound of Example 1-1 was used than in the case the drying agent of the Comparative Example 1 was used.

REFERENCE SIGNS LIST

1 . . . organic EL element, 2 . . . element substrate, 3 . . . sealing substrate, 4 . . . organic layer, 4a . . . hole-injection layer, 4b . . . hole transport layer, 4c . . . light-emitting layer, 4d . . . electron-transport layer, 5 . . . anode, 6 . . . cathode, 7 . . . filler, 8 . . . sealing agent

What is claimed is:

1. A compound represented by formula (1):

(1)

wherein M represents an aluminum atom, a titanium atom, a silicon atom, or a boron atom; m represents 1 or 2; n represents a positive integer; $R^1$, $R^2$ and $R^3$ each independently represent a C1-16 alkyl group optionally substituted with one or more fluorine atoms, or a C2-17 acyl group optionally substituted with one or more fluorine atoms, and in the case where a plurality of $R^3$ is present, the plurality of $R^3$ may be the same or different to each other;

a part of the carbon atoms composing the C1-16 alkyl group optionally substituted with one or more fluorine atoms may be replaced with one or more oxygen atoms, and a part of the carbon atoms composing the C2-17 acyl group optionally substituted with one or more fluorine atoms may be replaced with one or more oxygen atoms; and a proportion of a total number of the fluorine atoms in $R^1$, $R^2$ and $R^3$ is 15% or more relative to a total number of the fluorine atoms and hydrogen atoms in $R^1$, $R^2$ and $R^3$, and in the case where at least one of $R^1$, $R^2$ and $R^3$ is an acyl group substituted with one or more fluorine atoms, at least another one of $R^1$, $R^2$ and $R^3$ is an alkyl group substituted with one or more fluorine atoms.

2. The compound according to claim 1, wherein M is an aluminum atom.

3. The compound according to claim 1, wherein $R^1$, $R^2$ and $R^3$ are a C2-8 alkyl group substituted with one or more fluorine atoms.

4. A drying agent comprising the compound according to claim 1.

5. The drying agent according to claim 4, further comprising a viscosity modifier.

6. A sealing structure, wherein a pair of substrates is sealed with a sealing agent, and the sealing structure comprises the drying agent according to claim 4 therein.

7. An organic EL element comprising:

an element substrate;

a sealing substrate disposed opposite to the element substrate;

a laminate being provided on the element substrate and including an organic layer interposed between a pair of electrodes; and a sealing agent sealing outer peripheral parts of the element substrate and the sealing substrate;

wherein a sealed space is filled with the drying agent according to claim 4.

* * * * *